(12) United States Patent
Kitakaze et al.

(10) Patent No.: US 7,897,397 B2
(45) Date of Patent: Mar. 1, 2011

(54) CELL FUSION PROMOTER AND UTILIZATION OF THE SAME

(75) Inventors: Masafumi Kitakaze, Osaka (JP); Tetsuo Minamino, Osaka (JP); Akio Hirata, Osaka (JP)

(73) Assignees: Kowa Company, Ltd., Aichi (JP); Masafumi Kitakaze, Osaka (JP); Tetsuo Minamiao, Osaka (JP); Akio Hirata, Osaka (JP)

( * ) Notice: Subject to any disclaimer, the term of this patent is extended or adjusted under 35 U.S.C. 154(b) by 639 days.

(21) Appl. No.: 11/658,731

(22) PCT Filed: Jul. 12, 2005

(86) PCT No.: PCT/JP2005/012799
§ 371 (c)(1), (2), (4) Date: Oct. 23, 2007

(87) PCT Pub. No.: WO2006/011354
PCT Pub. Date: Feb. 2, 2006

(65) Prior Publication Data
US 2008/0287391 A1    Nov. 20, 2008

Related U.S. Application Data

(63) Continuation of application No. PCT/JP2005/012799, filed on Jul. 12, 2005.

(30) Foreign Application Priority Data

Jul. 27, 2004  (JP)  .............................. 2004-218243

(51) Int. Cl.
C12N 15/87   (2006.01)
C07H 21/02   (2006.01)
A61K 31/70   (2006.01)

(52) U.S. Cl. .................. 435/490; 536/25.2; 514/47
(58) Field of Classification Search ................... None
See application file for complete search history.

(56) References Cited

FOREIGN PATENT DOCUMENTS

JP    2005-506845 A    3/2005

OTHER PUBLICATIONS

Sigma Biochemicals and Reagents for Life Science Research Catalog, St. Louis, MO, 2002-2003, only pp. 82-83 supplied.*
M. Keresztes et al., "Basal and ATP-Stimulated Phosphoinositol Metabolism in Fusing Rat Skeletal Muscle Cells in Culture," Experimental Cell Research, vol. 196, pp. 362-364, 1991.
J. Nygren et al., "Bone Marrow-Derived Hematopoietic Cells Generate Cardiomyocytes at a Low Frequency Through Cell Fusion, but not Transdifferentiation," Nature Medicine vol. 10, No. 5, May 2004.
H. Nakajima and M. Komeda, Ischemic Heart Disease (IHD) Frontier vol. 4, No. 4, pp. 15-19, May 15, 2003.
H. Wada, et al., "Calcium/Calmodulin and Calcineurin Signaling is Involved in Cell Fusion between Adult Stem Cells and Cardiomyocytes", Circulation Journal, OE-359, vol. 68, Suppl. 1, p. 227, 2004.
Di Virgilio Francesco et al., "ATP Receptors and Giant Cell Formation", Journal of Leukocyte Biology, vol. 66, No. 5, Nov. 1999, pp. 723-726 (Nov. 1999).
Frank Natasha Y et al., "Regulation of Progenitor Cell Fusion by ABCB5 P-glycoprotein, a Novel Human ATP-Binding Cassette Transporter", Journal of Biological Chemistry, vol. 278, No. 47, pp. 47156-47165 (Nov. 21, 2003).
Alvarez-Dolado Manuel et al., "Fusion of Bone-Marrow-Derived Cells with Purkinje Neurons, Cardiomyocytes and Hepatocytes", Nature (London), vol. 425, No. 6961, pp. 968-973 (Oct. 30, 2003).
Prockop Darwin J. et al., "One Strategy for Cell and Gene Therapy: Harnessing the Power of Adult Stem Cells to Repair Tissues", Proceedings of the National Academy of Sciences of the United States of America, vol. 100, No. Supp 1, pp. 11917-11923 (Sep. 30, 2003).
Wagers A.J. et al., "Plasticity of Adult Stem Cells", Cell, Cell Press, Cambridge, MA, USA, vol. 116, No. 5, pp. 639-648 (Mar. 5, 2004).
Hori et al., Hypertension, 18(5):565-574 (1991).
Sanada et al., Japanese Society of Clinical Physiology Zasshi, 31(2):73-78 (2001).

* cited by examiner

*Primary Examiner* — Lawrence E Crane
(74) *Attorney, Agent, or Firm* — Peter F. Corless; Christine C. O'Day; Edwards Angell Palmer & Dodge LLP

(57) ABSTRACT

The present invention provides a regeneration promoter for regenerating tissue with the use of somatic stem cells. The invention also provides a cell fusion promoter comprising ATP or its metabolite which is safely usable in vivo, a method of producing fused cells in the presence of ATP or its metabolite and a related pharmaceutical composition for regenerating or improving the function of a tissue or an organ in a subject suffering from dysfunction or hypofunction due to injury or denaturation.

8 Claims, 4 Drawing Sheets

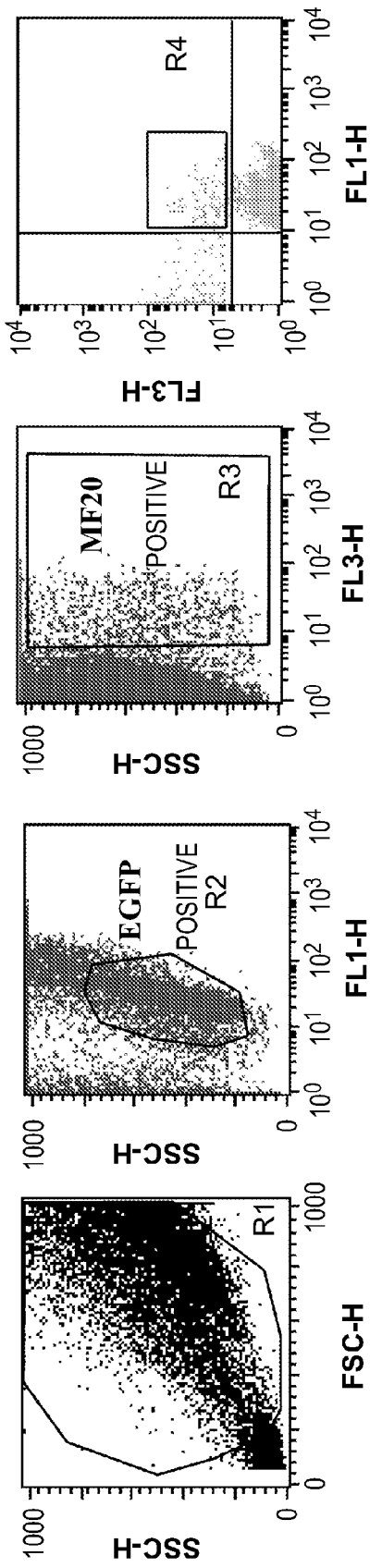

CELL FUSION PROMOTER AND UTILIZATION OF THE SAME

This application is a 371 national stage application of International application no. PCT/JP05/12799, filed on Jul. 12, 2005, which claims the prior benefit of Japanese application no. JP 2004-218243, filed on Jul. 27, 2004.

TECHNICAL FIELD

The present invention provides a cell fusion promoter composed of ATP or a metabolite thereof and relates to a cell fusion promoter including ATP or a metabolite thereof as active ingredient as well as a method of producing cells (fused cells) which includes fusing cells in the presence of ATP or a metabolite thereof.

The present invention also relates to a pharmaceutical composition for functional regeneration or improvement with a stem cell for dysfunction or hypofunction due to damage or degeneration of a living tissue or organ, which includes ATP or a metabolite thereof and a pharmaceutically acceptable carrier, use of ATP or a metabolite thereof for producing the same, and a therapeutic method of using the same.

BACKGROUND ART

Regeneration medicine has attracted attention as medical treatment for the purpose of regenerating a cell, tissue or organ lost due to a disease or accident; or of recovering the function thereof. Regeneration medicine also includes cell transplantation using living cells, such as skin transplantation and organ transplantation, and particularly in recent years, the technology of differentiating stem cells into cells having the function of each tissue thereby regenerating an organ or tissue which is not capable of spontaneous regeneration or recovering the function thereof has been developed, and generation medicine utilizing this technology attract attention.

Stem cells are juvenile, undifferentiated parent cells having self-regenerating ability as a source growing into a tissue or organ for replenishing cells approaching death. Embryonic stem cells (ES cells) derived from embryos attract attention, but cannot become autologous cells without nuclear transfer to somatic cells, thus causing immunological rejection upon transplantation and requiring necessity for genetic recombination, confirmation of HLA compatibility, and simultaneous use of an immunosuppressant. Attention is focused on utilization of somatic stem cells (tissue stem cells, organ stem cells) as autologous cells with no risk of immunologicals rejection. Accordingly, a method of separating mesenchymal stem cells from mammals (see patent document 1), a method of culturing the same (see patent document 2), and novel somatic stem cells (see patent document 3) have also been applied for patent.

Somatic stem cells are differentiated in such a predetermined direction that they are changed into tissue cells in which they occur, and thus it is considered difficult for somatic stem cells to regenerate tissues from which they cannot be collected, but it was nevertheless found that many somatic stem cells have the property of cellular differentiation which is different from their original differentiation. Such property is called the plasticity of somatic stem cells. For example, it came to be known that hematopoietic stem cells can be differentiated not only into blood cells but into any cells such as hepatocytes, skeletal muscle cells, neurons or the like. An approach to new regeneration medicine utilizing such property of somatic stem cells has been developed.

However, the regeneration of tissues or organs cannot be realized by merely administering such stem cells into the living body. For differentiation and growth of cells, the interaction of the cells with their ambient surroundings is very important, and the technology of constructing ambient surroundings suitable for stem cells administered (biomedical tissue technology) is necessary, so there still remain many problems for an approach to regeneration medicine. For example, a method of repairing tissues by introducing a temperature-dependent polymer gel composition containing adenosine phosphate and the like into the cartilages and other tissues in order to support cell proliferation for repairing and regenerating the tissues has also been applied for patent (see patent document 4).

With respect to the plasticity of somatic stem cells, there are two theories, one of which propounds that the plasticity is attributable to transdifferentiation and the other of which propounds that the plasticity is attributable to cell fusion. For example, Alvarez-dolado et al. showed that bone marrow-derived cells (BMDCs) are naturally fused in vitro with neuronal precursor cells, and reported that by bone-marrow transplant, BMDCs are fused in vivo with hepatocytes, brain Purkinje cells and myocardial cells to form fused multinuclear cells (see non-patent document 1). Vassilopoulos et al. reported that upon transplantation of bone marrow hematopoietic stemcells into the liver, the hematopoietic stemcells are fused with hepatocytes to regenerate the liver (see non-patent document 2). It is also reported that after hematopoietic stem cells were transplanted in the heart, the stemcells were not recognized to be transdifferentiated into myocardial cells in genetic study with a mouse having a reporter gene as a gene expressed specifically in myocardial cells (see non-patent document 3). The mechanism of the plasticity of somatic stem cells is examined from every viewpoint but is still not completely elucidated.

Although the mechanism of the plasticity of somatic stem cells is not elucidated, there is a revealed possibility of new therapeutic techniques utilizing somatic stem cell plasticity wherein somatic stem cells are fused with cells of an organ or tissue thereby restructuring a damaged area without causing any immunological rejection.

Heart failure is a life-threatening severe disorder. In heart failure resulting from partial necrosis of heart muscle, even if the heart failure is recovered, the heart muscle once necrotized cannot recover and the patient is at risk of recurrence. Particularly, patients with dilated cardiomyopathy having bad prognosis are increasing, but no established therapeutic method therefor is found. Cardiac transplantation is a prosperous therapy, but owing to shortage of donors, there is a limit to treatment.

Myocardial cells, soon after birth, become adult myocardial cells not having proliferating ability. The heart muscle, when necrotized by myocardial infarction or the like to form fiber tissue partially, will not be reproduced again. The heart muscle having fiber tissue formed becomes thinner, to fail to maintain the pumping ability of the heart, thus making maintenance of heart function difficult.

In recent years, it is attempted to regenerate heart function by transplanting cells directly into the heart with deterioration of heart function. As cells used in transplantation, it is reported to use the following cells: embryonic myocardial cells (see non-patent documents 4 and 5), skeletal muscle blast cells that are skeletal muscle progenitor cells (see non-patent documents 6 and 7), and bone marrow cells exposed to a demethylating agent 5-azacytidine (see non-patent document 8). In any of these reports, animal models are used, and clinical applications are also conducted. For example, Hamano et al. transplanted autologous bone marrow cells into 5 patients with ischemic heart disease. As a result, they has reported that amelioration of ischemic heart disease are recognized in 3 of 5 patients (see non-patent document 9). Strauer et al. injected autologous bone marrow cells by catheter into a site of cardiac infarction of patients with acute cardiac infarction. As a result, they has reported that after 3 months, shrinkage of the site of infarction and amelioration of heart function are recognized (see non-patent document 10).

Although the mechanism for amelioration of heat function by cell transplantation is unrevealed, the amelioration is estimated to be attributable to cell fusion from the above-mentioned genetic examination reporting that there was no recognized transdifferentiation into myocardial cells (see non-patent document 3). In myocardial cells and skeletal muscle cells, multinuclear cells are present, and in skeletal muscle cells, a large number of nuclei are present at the periphery of the cells, and in myocardial cells, 1 or 2 to 3 nuclei are present in the center of the cell.

Cell fusion is a technique used widely in production of antibody and the like, and in addition to viruses such as Sendai virus, compounds such as polyethylene glycol is used as compounds for inducing cell fusion. However, such cell fusion techniques are intended for in vitro use, and these cell fusion promoters when applied to in vivo regeneration medicine may cause fusion of organ cells other than the objective cells, which makes application to clinical medicine substantially very difficult. In restructure of a damaged site of an organ or tissue by cell fusion with stem cells, no chemical is known at present for promoting cell fusion of the organ or tissue with stem cells.

[Patent Document 1] Japanese Patent Application Laid-open (JP-A) No. 2003-052365
[Patent Document 2] JP-A No. 2003-052360
[Patent Document 3] JP-A No. 2004-024246
[Patent Document 4] JP-A No. 2004-501682
[Non-Patent Document 1] Alvarez-dolado, M., et al., Nature, 425, 968-973 (2003)
[Non-Patent Document 2] Vassilopoulos, G., et al., Nature, 422, 901-904 (2003)
[Non-Patent Document 3] Murry, C. E., et al., Nature, 428, 664-668 (2004)
[Non-Patent Document 4] Leor, J., et al., Circulation, 94, II332-II336 (1996)
[Non-Patent Document 5] Li, R. K., et al., Ann. Thorac. Surg., 62, 654-661 (1996)
[Non-Patent Document 6] Murry, C. E., et al., J. Clin. Invest., 98, 2512-2523 (1996)
[Non-Patent Document 7] Scorsin, M., et al., J. Thorac. Cardiovasc. Surg., 119, 1169-1175 (2000)
[Non-Patent Document 8] Tomita, S., et al., J. Thorac. Cardiovasc. Surg., 123, 1132-1140 (2002)
[Non-Patent Document 9] Hamano, K., et al., Jpn. Circ. J., 65, 845-847 (2001)
[Non-Patent Document 10] Strauer, B. E., et al., Circulation, 106, 1913-1918 (2002)

DISCLOSURE OF THE INVENTION

Problems to be Solved by the Invention

The present invention provides a regeneration promoter for regenerating a tissue by utilizing somatic stem cells. The present invention also provides a cell fusion promoter which can be used safely in the living body.

Although the mechanism of the plasticity of somatic stem cells is still not sufficiently elucidated, the theory that plasticity attributable to cell fusion is becoming dominant. In the process of differentiation and growth of somatic stem cells administered, cell fusion also has an advantage that cell fusion with surviving somatic cells makes it unnecessary to construct ambient surroundings suitable for somatic stem cells administered, for example an anchorage for forming tissue. Accordingly, if there were a cell fusion promoter usable safely in the living body, damaged living tissue would be regenerable by using various somatic stem cells. In particular, skeletal muscle cells and myocardial cells occur originally as multinucleate cells, so there is no particular problem in multinucleation of the cells by cell fusion.

The present invention provides a cell fusion promoter for regenerating damaged living tissue.

Means for Solving by the Problems

The present inventors examined fixation of stem cells to a damaged site in regeneration medicine using stem cells, and focused attention on the fact that cell fusion is suitable as a method of fixing stem cells to a damaged site without constructing ambient surroundings suitable for stem cells, that is, without constructing an anchorage for fixing the cells, and they further extensively studied cell fusion. As a result, the inventors found that ATP or a metabolite thereof promotes cell fusion, particularly cell fusion between somatic cells and stem cells.

That is, the present invention provides a cell fusion promoter including ATP or a metabolite thereof and relates to a cell fusion promoter including ATP or a metabolite thereof as an active ingredient. The present invention also relates to a method of producing fused cells in the presence of ATP or a metabolite thereof.

The present invention also relates to a pharmaceutical composition for functional regeneration or improvement with a stem cell for dysfunction or hypofunction due to damage or degeneration of a living tissue or organ, which includes ATP or a metabolite thereof and a pharmaceutically acceptable carrier. Further, the present invention relates to use of ATP or a metabolite thereof for producing a pharmaceutical composition for functional regeneration or improvement with a stem cell for dysfunction or hypofunction due to damage or degeneration of a living tissue or organ, which includes ATP or a metabolite thereof and a pharmaceutically acceptable carrier. Furthermore, the present invention relates to a method of treating a disease based on dysfunction or hypofunction due to damage or degeneration of a living tissue or organ, which includes administering an effective amount of a pharmaceutical composition including ATP or a metabolite thereof and a pharmaceutically acceptable carrier to a patient with the disease.

In the present invention, the action of ATP in cells is revealed for the first time, and the promoting action of ATP or a metabolite thereof on cell fusion has been revealed. The cell fusion is not only useful for production of monoclonal antibody but also very useful for regeneration of a living tissue or organ, and the utilization of cell fusion in regeneration and growth of somatic cells has been expected particularly since the plasticity of somatic stem cells was found in recent years.

The present invention provides a cell fusion promoter for in vitro or in vivo cell fusion, and any substances used as the active ingredient of the present invention are highly safe substances produced in the living body, thus significantly contributing to the medical field utilizing cell fusion and antibody manufacturing field.

Many of muscular cells such as myocardial cells occur as multinucleate cells, and the fused cells produced by the method of the present invention can be used directly as cells in the living body, and thus the present invention is extremely useful for regeneration medicine, particularly regeneration medicine for myocardial cells.

BRIEF DESCRIPTION OF DRAWINGS

FIGS. 2A-D are graphs of fluorescence-immunostained co-cultured myocardial cells and bone marrow cells analyzed by flow cytometry.

BEST MODE FOR CARRYING OUT THE INVENTION

Figure 1A:
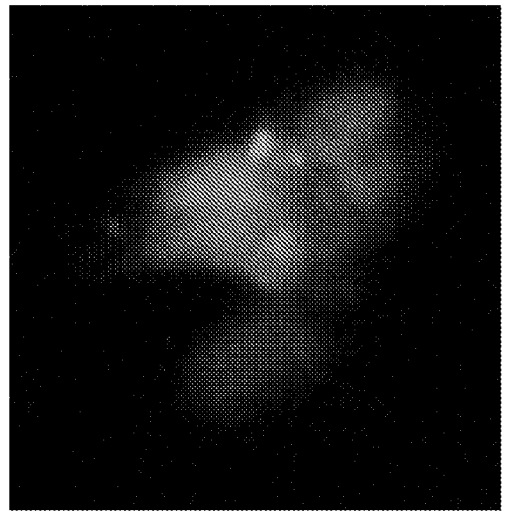
FIGS. 1A-C are photographs of fluorescence-immunostained co-cultured myocardial cells and bone marrow cells observed under a fluorescence microscope.

ATP or a metabolite thereof in the present invention includes ATP (adenosine 5'-triphosphate) or substances recognized as metabolites or homologues thereof in the living body, such as ADP (adenosine 5'-diphosphate), AMP (adenylic acid), 5'-inosinic acid or the like. An ingredient including ATP or one or more metabolites thereof can be used, and usually ATP is easily and preferably used. ATP or a metabolite thereof in the present invention may form a salt, and the salt is not particularly limited insofar as it is pharmaceutically acceptable. The salt of ATP or a metabolite thereof is preferably an alkali metal salt such as sodium salt or potassium salt or an alkaline earth metal salt such as magnesium salt or calcium salt.

The cell fusion promoter of the present invention includes the above-mentioned ATP or a metabolite thereof as an active ingredient and can be used if necessary as a cell fusion promoting composition comprising ATP and a metabolite thereof and a carrier acceptable in treatment of cell fusion. The cell fusion promoter and/or cell fusion promoting composition of the present invention can be used by adding it to a medium in which cells are to be fused or administering it to the living body.

The method of producing fused cells in the presence of ATP or a metabolite thereof in the present invention can be carried out by adding or administering ATP or a metabolite thereof in the present invention or the cell fusion promoter or the cell fusion promoting composition, under usual conditions of cell fusion. The added or administered amount is not particularly limited in such a range as not to cause side effects on cells. ATP or its metabolite itself in the present invention is a substance capable of being present under usual conditions in the living body. The substance can thus be used in a large amount with less toxicity, and is used usually by adding it to a cell fusion medium at a concentration of preferably 0.01 mM to 100 mM, 0.01 mM to 10 mM, 0.1 mM to 10 mM, or 0.1 mM to 3 mM, more preferably 1 mM to 3 mM.

The cells used in the cell fusion of the present invention can include various cells such as microbial cells, plant cells and animal cells, preferably animal cells, more preferably mammalian cells. The cell fusion of the present invention also includes cell fusion between immune cells and cancer cells, preferably cell fusion between somatic cells and stem cells. As the stem cells, either embryonic stem cells or somatic stem cells can be used, but from the viewpoint of using autologous cells, somatic stem cells are preferably used. The somatic stem cells may be any of mesenchymal stem cells, hematopoietic stem cells and neural stemcells, but bone marrow cells are preferable for the reason of availability. The objective stem cells can be selected by purifying and separating bone marrow cells prior to use.

In the cell fusion of the present invention, the cells to be fused are not particularly limited and may be either cells outside the living body or cells inside the living body, and cells derived from various living tissues or organs include, for example, those from tissues or organs such as nerve, muscle (smooth, striated, cardiac), bone, cartilage, liver, kidney, pancreas, respiratory epithelium, hematopoietic cell, spleen, skin, hair, tooth, cornea, stomach and intestine, for example, hepatocyte, osteocyte, blood cell, immune cell, neurocyte, skeletal muscle cell and myocardial cell. The cell formed by the cell fusion of the present invention is a binucleated cell, and thus the fusion cell is preferably a cell capable of surviving as a binucleate cell and exhibiting the objective function. Such cells include immune cell, skeletal muscle cell and myocardial cell.

In the case of immune cells for example, specific immune cells can be fused in vivo or in vitro by the method of the present invention, then induced for differentiation, and anchored to a site induced to be differentiated in the living body.

Skeletal muscle cells are subjected to cell fusion in the present invention in a site with a decrease in skeletal muscle cells, thereby regenerating decreased skeletal muscles and usefully serving for treatment of diseases such as muscular dystrophy. Myocardial cells can be subjected to cell fusion in the present invention in a site with deterioration of heart function due to such as cardiac infarction, thereby regenerating or improving heart function.

By the cell fusion of the present invention, the plasticity of stem cells can also be utilized. For example, a myocardial cell can be fused with a hematopoietic stem cell to regenerate a binucleate myocardial cell.

The cell fusion of the present invention enables easy and rapid regeneration in vitro or in vivo of fused cells having bodily functions thereby repairing or ameliorating dysfunction or hypofunction in various tissues or organs. Particularly, skeletal muscle cells and myocardial cells are originally multinucleate cells, thus making cell fusion easy and facilitating the cell fusion of the present invention without establishing any particular conditions for cell fusion. The formed binucleate cells are similar to the original multinucleate cells and can retain the function of the same kind.

A method of mixing and culturing two kinds of cells to be fused with each other is convenient and preferable as the method of cell fusion in vitro in the present invention. When conducted in vivo, the method of the invention can be carried out by transplanting cells to be fused, for example somatic stem cells such as bone marrow cells, into a site where dysfunction or hypofunction occurs due to damage or degeneration of a living tissue or organ, followed by adding or administering the invented composition containing an active ingredient composed of ATP or a metabolite thereof thereto.

In a site with much blood stream such as in heart, a somatic stem cell contained in blood, such as hematopoietic stem cell, can be used as it is. In this case, the present composition containing an active ingredient composed of ATP or a metabolite thereof can be added or administered to the site where dysfunction or hypofunction occurs due to damage or degeneration of a living tissue or organ.

In this case, the amount of ATP or a metabolite thereof used in the present invention is regulated preferably such that the concentration of ATP or a metabolite thereof becomes 0.01 mM to 100 mM, 0.01 mM to 10 mM, 0.1 mM to 10 mM, or 0.1 mM to 3 mM, or 1 mM to 3 mM, in the site where dysfunction or hypofunction occurs due to damage or degeneration of a living tissue or organ.

The living tissue or organ in the present invention includes muscle, immune system, liver, heart, bone, cartilage, joint and the like, preferably heart and muscle where multinuclear cells occur. The damage or degeneration in the present invention include every kind of deformation such as defect, damage, denaturation, deformity and the like in cells that should originally occur. When the functions of surrounding normal cells are disturbed by damage or degeneration, these degenerated cells are preferably removed prior to the cell fusion of the present invention.

The dysfunction or hypofunction of the present invention encompasses every dysfunction or hypofunction where in the whole or a part of the original function of a living tissue or organ is arrested as a whole or decreased quantitatively. Application of the method of the present invention to the case where a part of such function is decreased encompasses not only therapy but also prophylaxis.

The "pharmaceutically acceptable carrier" in the pharmaceutical composition of the present invention includes a vehicle, a diluent, a filler, a disintegrating agent, a stabilizer, a preserver, a buffering agent, an emulsifier, an aromatic substance, a coloring agent, a sweetener, a viscous substance, a flavoring substance, a solubilizing agent, and other additives. By using at least one of such carriers, pharmaceutical compositions can be prepared in the form of tablets, pills, powder, granules, injection, liquid, capsules, troches, liquid, suspension or emulsion. These pharmaceutical preparations can be administered orally or parenterally, and parenteral administration is preferable. The pharmaceutical composition of the present invention is administered preferably by a method of direct injection into a tissue or organ by intravenous injection, injection by catheter, or a surgical method.

The amount of the pharmaceutical composition of the invention administered varies depending on the age, sex, weight and symptom of the patient, therapeutic effect, administration method, treatment time, and the type of the active ingredient contained in the pharmaceutical composition, but is usually in the range of 1 mg to 5000 mg, preferably 10 mg to 1000 mg, per adult for each administration. However, the amount of the pharmaceutical composition administered varied depending on various conditions, and thus an amount lower than the above amount may be sufficient in some cases or an amount higher than the above range may be necessary in other cases. Particularly the injection can be produced by dissolving or suspending the active ingredient at a concentration of 0.1 µg/ml to 10 mg/ml in a nontoxic pharmaceutically acceptable carrier such as physiological saline or commercial distilled water for injection.

The injection produced in this manner can be administered once or several times per day to a patient in need of treatment in an amount of 50 µg to 100 mg, preferably 200 µg to 50 mg, per kg for each administration. Depending on the case, the injection can also be prepared as a non-aqueous diluent (for example, propylene glycol, polyethylene glycol or vegetable oil such as olive oil, or an alcohol such as ethanol), a suspension or an emulsion. Aseptization of such injection can be carried out by sterilization through filtration with a bacteria-retaining filter, by compounding the injection with a sterilizing agent, or by irradiation. The injection can be produced in a form to be reconstituted at use. That is, a sterile solid composition can be prepared by a freeze-drying method and dissolved in sterile distilled water for injection or in another solvent prior to use.

The disease to which the regeneration medicine in the present invention is expected to be applicable includes nervous system disorders such as Parkinson's disease, marrow damage and Alzheimer's disease, cardiovascular disease such as cardiac infarction and dilated cardiomyopathy, cutaneous diseases such as burn injury, traumatic cutaneous defect and bedsore, bone diseases such as traumatic bony defect, traumatic cartilage defect, osteoporosis and periodontal disease, and cataract, and the present invention is applied particularly preferably to ischemic or non-ischemic heart diseases with decreased left ventricular function, such as cardiac infarction and dilated cardiomyopathy.

Hereinafter, the operation of the invention is described in more detail, which is set forth for understanding of the invention and not intended to limit the technical scope of the invention.

From a 1- to 2-day-old Wistar-Kyoto rat, the heart was removed, and myocardial cells were isolated therefrom and cultured. Bone marrow mononuclear cells separated from the bone marrow of an EGFP (enhanced green fluorescent protein) transgenic rat were introduced into the myocardial cells, followed by co-culture thereof.

Figure 1B:
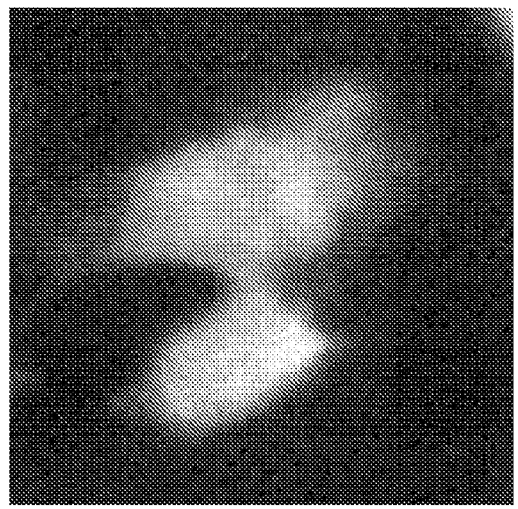
Figure 1C:
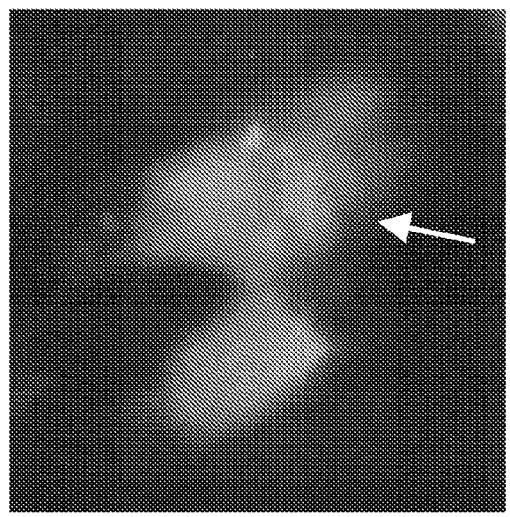
Figure 3A:
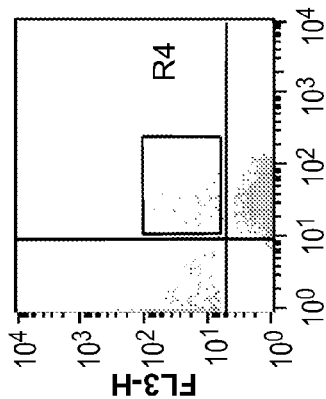
FIGS. 3A-D are graphs showing the results of groups of myocardial cells and bone marrow cells to which 0 mM, 1 mM, 2 mM or 3 mM ATP were added at the time of co-culture thereof, as analyzed by the same flow cytometry as in FIG. 2.
Figure 3B:
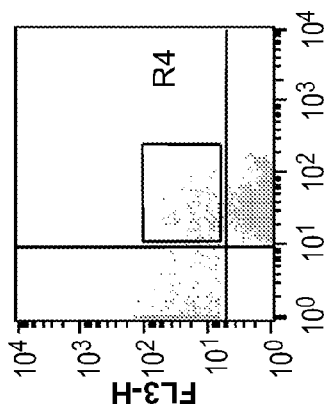
Figure 3C:
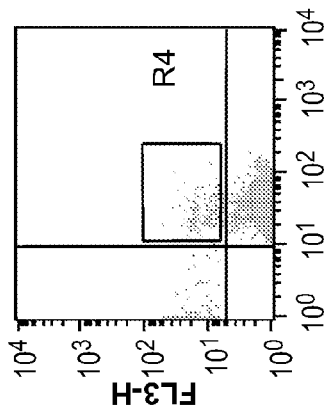
Figure 3D:
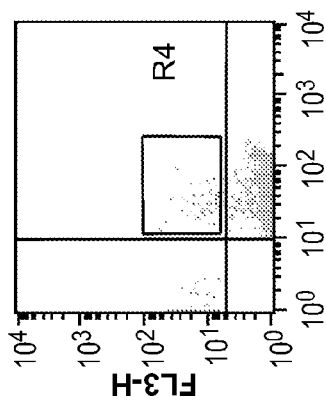

One week after co-culture, the cells were fixed with paraformaldehyde and then fluorescence-immunostained with MF20 (red) as myocardial cell-specific primary antibody and R-PE conjugated anti-mouse Ig antibody as secondary antibody and observed under a fluorescence microscope. The resulting photographs are shown in FIGS. 1A-C. In FIG. 1, (A) is a photograph where a PE filter was used, (B) is a photograph where a FITC filter was used, and (C) is a photograph where a PE/FITC double filter was used. The myocardial cells are MF 20-positive and shown in red, and the bone marrow cells are EGFP-positive and thus shown in green. As shown in the arrowed cells in (C) in FIG. 1, fused cells positive to both MF20 and EGFP were recognized.

Flow cytometry was used to quantitatively determine the number of these fused cells. The cells were fixed with paraformaldehyde in the same manner as above, then fluorescence-immunostained in a suspended state with primary antibody MF20, a biotin-conjugated anti-mouse antibody as secondary antibody and a streptavidin/PerCP-cye5.5 conjugate as tertiary antibody, and analyzed by flow cytometry. 50,000 cells were analyzed for each analysis. The results are shown in the graphs in FIGS. 2A-D. In FIG. 2, (A) shows cells in R1 gate, (B) shows cells in R2 gate, (C) shows cells in R3 gate, and (D) shows cells in R4 gate. The cells in the gate R4 in FIG. 2 (D) were confirmed to be fused cells positive to both MF20 and EGFP.

Then, according to a similar manner to that described above, ATP was added at a concentration of 0 mM (control), 1 mM, 2 mM and 3 mM respectively to the myocardial cell/bone marrow cell co-culture system, and the number of fused cells was examined. Each group at the predetermined concentration of ATP was stained in the same manner as in FIG. 2 and analyzed by flow cytometry. The results are shown in the graphs in FIGS. 3A-D.

Figure 4:
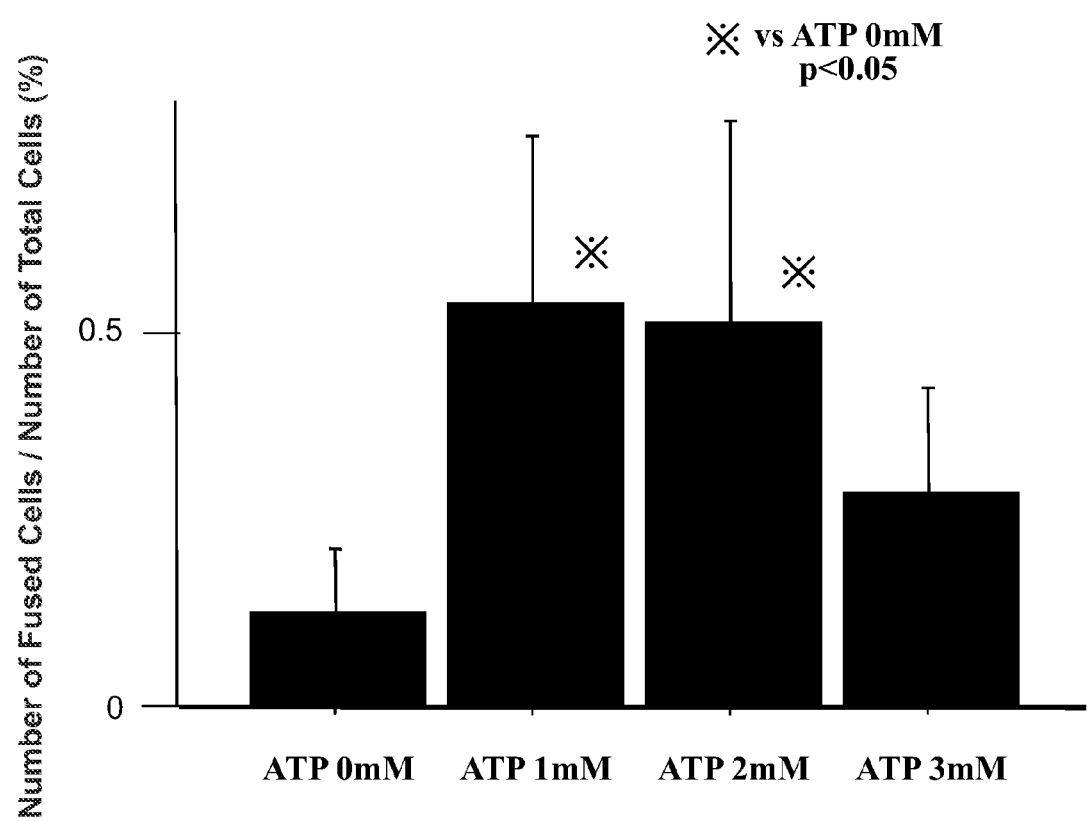
FIG. 4 is a graph showing the ratio (%), based on the result in FIG. 3, of the number of fused cells to the total number of cells in each group to which ATP was added.

From these results, the ratio of fused cells (cells in the R4 gate) to the total number of cells was calculated. The result is shown in the graph in FIG. 4. In FIG. 4, the ratio (%) of the number of fused cells to the total number of cells is shown on the ordinate, and the concentration of ATP (0 mM, 1 mM, 2 mM and 3 mM) is shown on the abscissa. The asterisk (*) in FIG. 4 indicates significance ($p<0.05$) relative to the control group. As a result, it was confirmed that only about 0.1% fused cells were formed in the control group in the absence of ATP, while about 0.5% fused cells that are about 5-times as much as in the control group were formed in the group to which 1 or 2 mM ATP had been added. In the group to which 1 or 2 mM ATP had been added, the ratio of the number of fused cells was increased significantly as compared with the control group.

Hereinafter, the present invention is described in more detail by reference to the Examples, but the present invention is not limited by the Examples.

EXAMPLE 1

According to the method of Minamino et al. (Minamino T., Gaussin V., DeMayo F. J., et al., Circ. Res. 2001; 88:587-592), the heart was removed from a 1- to 2-day-old Wistar-Kyoto rat and myocardial cells were isolated. The resulting myocardial cells were plated at a density of $10^5$ cells/cm$^2$ onto each well of a 6-well plate and cultured in a DMEM medium containing 10% FCS and penicillin-streptomycin.

Separately, the bone marrow was collected from the thigh bone and shin bone of a 8-week-old, EGFP (enhanced green fluorescent protein) transgenic rat (Nippon SLC), and according to the method of Terada et al. (Naohiro Terada, Takashi Hamazaki, MasahiroOka, et al., Nature 2002; 416:542-545), its mononuclear cell component only was separated by the percoll method. The resulting marrow mononuclear cells were re-suspended in a DMEM medium containing 10% FCS and penicillin-streptomycin. This suspension was put to the above 6-well plate on the second day of culture of the myocardial cells such that $10^6$ marrow mononuclear cells were added to each well, followed by co-culture of the cells.

After one week of co-culture, the cells were isolated individually with 0.08% trypsin, spread onto, and bonded with, a 2-well Lab-Tek chamber slide, fixed with 4% paraformaldehyde, treated with 0.1% Triton X-100, fluorescence-immunostained with myocardial cell-specific primary antibody MF20 (red) and R-PE conjugated anti-mouse Ig's antibody (BIOSOURCE) as secondary antibody, and observed under a fluorescence microscope. The result is shown in FIG. 1. As shown in the arrowed cells in FIG. 1 (C), fused cells positive to both MF20 and EGFP were recognized.

Then, the number of the fused cells was quantitatively determined by flow cytometry. After 1 week of co-culture, the cells were treated with trypsin and fixed with paraformaldehyde in the same manner as above, fluorescence-immunostained in a suspended state with primary antibody MF20 (labeled with PerCP-cye5.5 and captured as being positive to FL-3), biotin-conjugated anti-mouse Ig's antibody (BD Pharmingen) as secondary antibody, and streptavidin/PerCP-cye5.5 conjugate (BD Pharmingen) as tertiary antibody, and analyzed by flow cytometry. The result is shown in FIG. 2. 50,000 cells were analyzed for each analysis. The bone marrow cells were EGFP-positive and thus captured as FL-1-positive, and the cells in the gate R4 in FIG. 2 (D) were confirmed to be fused cells positive to both MF20 and EGFP.

EXAMPLE 2

ATP was added at a concentration of 0 mM (control), 1 mM, 2 mM and 3 mM respectively to each well in the myocardial cell/bone marrow cell co-culture system shown in Example 1, and the number of fused cells was examined in the same manner as in Example 1. On the 3rd day and 5th day of co-culture, floating cells were collected and the medium was exchanged with fresh one containing ATP at the predetermined concentration.

The number of the fused cells was quantitatively determined by flow cytometry. After 1 week of co-culture, the cells were treated with trypsin and fixed with paraformaldehyde in the same manner as in Example 1, fluorescence-immunostained in a suspended state with primary antibody MF20 (labeled with PerCP-cye5.5 and captured as being positive to FL-3), biotin-conjugated anti-mouse Ig's antibody (BD Pharmingen) as secondary antibody, and streptavidin/PerCP-cye5.5 conjugate (BD Pharmingen) as tertiary antibody, and analyzed by flow cytometry. The result is shown in FIG. 3. 50,000 cells were analyzed for each analysis. The bone marrow cells were EGFP-positive and thus captured as FL-1-positive, and the cells in the gate R4 in FIG. 3 (D) were confirmed to be fused cells positive to both MF20 and EGFP. The number of the fused cells in the group to which 1 mM or 2 mM ATP had been added was confirmed to be higher than in the control group.

The percentage (%) of the fused cells in the total cells in each of the analyzed groups is shown in a graph. The results are shown in FIG. 4. In the group to which 1 or 2 mM ATP had been added, the ratio of the number of fused cells was increased significantly as compared with the control group.

INDUSTRIAL APPLICABILITY

The present invention provides a composition having a promoting action on cell fusion and is useful in the industrial field utilizing cell fusion for example the antibody manufacturing field and the pharmaceutical field and is industrially applicable.

The invention claimed is:

1. A method for producing fused cells which comprises:
   causing the fusion of a stem cell and a somatic cell in an ex vivo cell culture following the addition of a sufficient quantity of ATP to said culture.

2. The method according to claim 1, wherein the stem cell is a somatic stem cell.

3. The method according to claim 2, wherein the somatic stem cell is a bone marrow cell.

4. The method according to claim 1, wherein the somatic cell is a myocardial cell.

5. The method according to claim 1, wherein the concentration of ATP is between 1 mM-3 mM.

6. A method of producing fused cells in an in vitro cell culture which comprises:
   a) providing an in vitro cell culture containing at least one stem cell and at least one somatic cell;
   b) administering ATP in an amount sufficient to produce a concentration of between 1 mM and 3 mM in said in vitro culture;
   thereby producing at least one fused cell in an in vitro culture.

7. The method according to claim 6, wherein the stem cell is a bone marrow cell.

8. The method according to claim 7, wherein the somatic cell is a myocardial cell.

\* \* \* \* \*